United States Patent [19]

Takagishi et al.

[11] 4,402,692
[45] Sep. 6, 1983

[54] MEDICAMENT CAPSULES FOR RECTAL APPLICATION

[75] Inventors: Yasushi Takagishi, Nishinomiya; Yoshio Doi, Ibaraki; Kanji Aita, Minoo; Noboru Hoshi, Higashi-Kurume, all of Japan

[73] Assignees: Shionogi & Co., Ltd., Osaka; Shin-Etsu Chemical Co., Ltd., Tokyo, both of Japan

[21] Appl. No.: 269,706

[22] Filed: Jun. 2, 1981

[30] Foreign Application Priority Data

Jun. 5, 1980 [JP] Japan ................................ 55-76264

[51] Int. Cl.³ .............................................. A61M 7/00
[52] U.S. Cl. ................................................... 604/890
[58] Field of Search ..................... 128/260; 424/19–24; 604/890–894

[56] References Cited

U.S. PATENT DOCUMENTS 4,250,163 2/1981 Nagai et al. .......................... 128/260
4,298,003 11/1981 Theeuwes et al. ................... 128/260

Primary Examiner—Richard J. Apley
Assistant Examiner—T. J. Wallen
Attorney, Agent, or Firm—Toren, McGeady and Stanger

[57] ABSTRACT

The invention provides a novel and efficient means for the administration of a therapeutically effective ingredient by rectal application in the form of a medicament capsule encapsulating the effective ingredient. The medicament capsule according to the invention is formed of a hard capsule shell made of a mixed ester of a cellulose ether, e.g. alkyl-, hydroxyalkyl- and hydroxyalkyl alkylcelluloses, esterified with aliphatic monacyl groups and acidic succinyl groups. When the capsule is inserted into the rectum, the capsule shell is disintegrated and the rectally absorbable effective ingredient is readily and smoothly released into the rectum and absorbed to exhibit therapeutical effects as efficiently as with conventional suppositories.

7 Claims, 2 Drawing Figures

MEDICAMENT CAPSULES FOR RECTAL APPLICATION

BACKGROUND OF THE INVENTION

The present invention relates to a novel medicament capsule for rectal application. More particularly, the invention relates to a medicament form of a hard capsule made of a novel enterosoluble cellulose derivative encapsulating a therapeutically effective ingredient capable of being absorbed through the rectum.

As is well known, a variety of medicines are used in a medicament form suitable for rectal application with an object either to obtain a systemic action or to obtain a local action of the effective ingredient. Several of the examples of the medicaments of which a systemic action is desired by the rectal application include antipyretic, anodynic and antiphlogistic agents such as aspirin, aminopyrine, sulpyrin, phenylbutazone, oxyphenbutazone, indometacin and the like, antispasmodic agents such as butyl scopolamine bromide and the like, antibiotics such as erythromycin and the like, anti-tuberculosis agents such as ethionamide and the like, and others. Those medicines of which a local action is desired include, on the other hand, astrigents, local anesthetics and bactericidal agents with or without admixture of an adrenocortical hormone for haemorrhoids.

At any rate, the effective ingredient in the medicine administrated by rectal application is directly absorbed in the venous plexus of the rectum to be distributed throughout the body by the blood circulation without passing the portal vein and the liver. Therefore, a rectally applicable medicament form is preferable particularly for the medicines of which the effective ingredient causes a disorder in the stomach when orally administrated or the ingredient is susceptible to decomposition in the digestive tract or in the liver resulting in decreased effectiveness of the medicine.

As is well known, the medicament forms for rectal application in general include suppositories ans so-called rectal capsules.

Suppositories as a medicament form are prepared usually by dispersing the therapeutically active ingredient in a base such as cacao butter, polyethyleneglycol, mixture of higher fatty acid glycerides and the like solidifying and shaping the blend into a desired form, e.g. a conical or cannonball-like form, suitable for insertion into the coelom through the anus. Suppositories are the most widely used medicament form for rectal application and effective by releasing the effective ingredient in the rectum when melted at the body temperature or dissolved in the rectal fluid.

Suppositories present a very convenient means for rectal application of the medicine but not without various problems in the preparation and storage thereof. Several of the problems are that an efficient means is required for the uniform dispersion of the effective ingredient in the highly consistent suppository base, that suppositories are not a suitable medicament form for an ingredient susceptible to thermal decomposition because the ingredient must be distributed in the base molten by heating, that suppositories must be stored in a cool place because deformation of suppotitories is unavoidable at a relatively high temperature and that specific facilities are necessary for the preparation thereof to be in compliance with the aforementioned problems.

On the other hand, a rectal capsule is a modification of the suppository in a sense and can be prepared in a manner similar to the preparation of soft capsules. That is, the therapeutically effective ingredient, alone or with admixture of other additives according to need, is shaped by lightly compressing and encapsulated and further shaped with a capsule base such as gelatin. Therefore, preparation of rectal capsules also requires specific facilities and skillful works.

In view of the above problems in the rectal capsules, it is another possible way to utilize an ordinary gelatin-made capsule for oral administration as the medicament form for retal application. Several difficulties are, however, encountered in the use of gelatin capsules for rectal application. For example, medicines with acidity or in an aqueous liquid form cannot be encapsulate in both hard and soft gelatin-made capsules. Further, powdery medicines encapsulated in an soft capsule are not free from the problem in the stability in addition to the burdensomeness in the preparation of the medicament form.

Accordingly, it has been eagerly desired to develop a medicament capsule for rectal application easy to prepare into the medicament form with excellent stability during storage and capable of uniform disintegrability in the rectum and the absorbability of the effective ingredient through the rectum.

SUMMARY OF THE INVENTION

Thus an object of the present invention is to provide a very convinient and reliable method for the administration of a rectally absorbable therapeutically effective medicament in a form of a capsule for rectal application.

Another object of the invention is to provide a novel and improved medicament capsule for rectal application with which the problems in the conventional suppositories and rectal capsules as well as the problems involved in the application of ordinary hard or soft capsules to the rectal use are completely solved.

The medicament capsule for rectal application according to the present invention comprises (a) a hard capsule shell made of a mixed ester of a cellulose ether etherfied by hydroxy-substituted and/or unsubstituted alkyl groups and esterified with aliphatic monoacyl groups and acidic succinyl groups and (b) a therapeutically effective ingredient capable of being rectally absorbed and encapsulated in the said hard capsule shell.

DETAILED DESCRIPTION OF THE PREFERRED EMBODIMENTS

Figure 1:
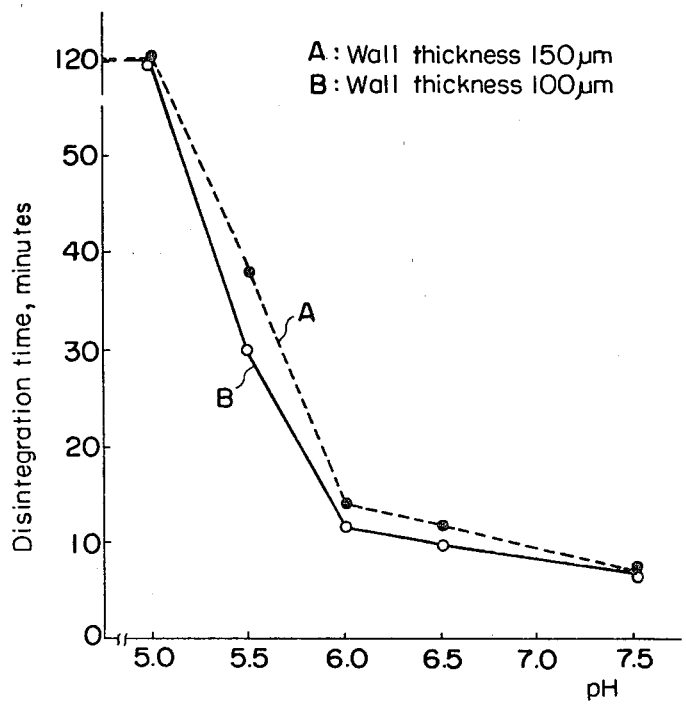
FIG. 1 shows the disintegration time of the inventive capsules in the test solutions as a function of the value of pH of the solution.

The hard capsule shell used in the inventive medicament capsule for rectal application is shaped of the above mentioned enteric cellulose derivative and has many advantages, in addition to the excellent enterosolubility, of the intoxicity to the living body and the chemical stability in the lapse of time without the danger of producing any toxic or harmful decomposition products during storage as well as excellent physical stability over a long period of time to retain the mechanical properties such as pliability even without formulation of a plasticizer.

The enteric cellulose derivative for shaping the shell of the inventive medicament capsule is a mixed ester of a cellulose ether substituted or etherified by alkyl groups and/or hydroxyalkyl groups and esterified by aliphatic monoacyl groups and acidic succinyl groups. The preparation of such a mixed ester of cellulose ether is described, for example, in U.S. Pat. No. 4,226,981. Several of the advantages obtained with this type of cellulose derivatives are as follows.

(1) The cellulose derivative can form a film having high pliability by use of no or a very small amount of a plasticizer.

(2) The films thus formed do not stick to each other.

(3) The cellulose derivative is chemically and physically stable without deterioration over a long period of time even in a highly humid and hot atmosphere.

(4) The purification process of the esterified products after completion of the reaction can be performed easily so that the purified products of the cellulose derivative contain no undesirable impurities.

As is mentioned above, the mixed ester of the cellulose ether used for shaping the capsule shell has two kinds of esterifying substituent groups; i.e. aliphatic monoacyl groups represented by the general formula R—CO—, in which R is a monovalent aliphatic group or, in particular, an alkyl group, and acidic succinyl groups expressed by the formula HO—CO—CH$_2$CH$_2$—CO— bonded to the cellulose ether through ester linkages and obtained by the esterification reaction of a cellulose ether with succinic anhydride and anhydride of an aliphatic monocarboxylic acid.

The cellulose ether above mentioned has necessarily alkyl groups and/or hydroxyalkyl groups as the substituent groups bonded to the glucose residue through ether linkages and is exemplified by alkylcelluloses such as methylcellulose, ethylcellulose, propylcellulose and the like, hydroxyalkylselluloses such as hydroxyethylcellulose, hydroxypropylcellulose, hydroxybutylcellulose and the like, hydroxyalkyl alkylcelluloses such as hydroxyethyl methylcellulose, hydroxyethyl ethylcellulose, hydroxypropyl methylcellulose, hydroxypropyl ethylcellulose, hydroxybutyl methylcellulose, hydroxybutyl ethylcellulose and the like as well as those cellulose ethers having two kinds or more of the hydroxyalkyl groups such as hydroxyethyl hydroxypropylcellulose, hydroxyethyl hydroxybutylcellulose, hydroxyethyl hydroxypropyl methylcellulose and the like.

These cellulose ethers are not particularly limitative in respect of the molecular weight and the degree of substitution by the alkyl groups and/or hydroxyalkyl groups. When the cellulose ether is an alkylcellulose or a hydroxyalkyl alkylcellulose, however, it should be noted that difficulty in the esterification reaction with the above mentioned acid anhydrides is increased if the degree of substitution by the alkyl groups is excessively large over a limit of, say, 2.5 alkyl groups per glucose residue.

The anhydride of the aliphatic monocarboxylic acid used in the esterification of the cellulose ether in combination with succinic anhydride is exemplified by the anhydrides of acetic, propionic, butyric and valeric acids. These acid anhydrides as well as succinic anhydride may not be of special grades and commercially available ones can be used without further purification.

The esterification reaction of the cellulose ether with the acid anhydrides is carried out in several different ways. For example, the cellulose ether and the acid anhydrides are reacted in a carboxylic acid such as acetic acid, propionic acid, butyric acid and the like as the reaction medium in the presence of an alkali metal salt of a carboxylic acid such as sodium acetate, potassium acetate and the like as a catalyst. Alternatively, the reaction is carried out in a suitable organic solvent such as dimethylformamide, acetone and the like in the presence of a basic catalyst such as $\alpha$-picoline, pyridine and the like.

The average degrees of substitution per glucose unit by the acidic succinyl groups and the aliphatic acyl groups are determined in accordance with the desired performance of the mixed ester product as well as the type of the cellulose ether as the starting material. Generally speaking, the average numbers of the substituent groups are desirably at least 0.1 and at least 0.05 per glucose unit for the acidic succinyl groups and the aliphatic monoacyl group, respectively, since smaller degrees of substitution result in unsatisfactory pliability and enteric solubility of the cellulose derivative.

The shaping procedure of the capsule shells from the above described cellulose derivative is rather conventional and may be performed by the dipping method using molding pins. Thus, the cellulose derivative is dissolved in a suitable solvent which is an organic solvent or a mixture of an organic solvent and water into a dipping solution of an adequate concentration and, after defoaming, if necessary, a molding pin is dipped therein and then pulled up gradually so as that the viscous film of the solution adhering to the molding pin is dried and converted to a solid film of the form of a capsule shell, which is detached from the molding pin followed, if necessary, by finishing to give a capsule shell of the desired size and form.

The organic solvent used for the preparation of the above mentioned dipping solution is exemplified by methyl alcohol, ethyl alcohol, acetone, ethyleneglycol monomethyl ether, ethyleneglycol monoethyl ether, ethyl acetate and the like, which may be used either alone or in combination of two kinds or more. The concentration of the dipping solution is of course determined in consideration of the workability in the shaping procedure by the dipping method as well as the desired wall thickness of the finished capsule shells. Usually, capsule shells of a smaller wall thickness are prepared by use of a less concentrated solution and the concentration should be increased when capsule shells of a larger wall thickness are to be prepared. The wall thickness of the capsule shells is usually in the range from 100 to 150 $\mu$m or, preferable from 100 to 120 $\mu$m in consideration of the balance of the bioavailability of the effective ingredient contained therein and the physical properties of the capsules.

The dipping solution may be formulated with admixture of several conventional additives according to need such as coloring agents, taste- and flavor-improvers, flavors, plasticizers and the like, Needless to say, the amounts of these optional additives to be added to the dipping solution are limited not to adversely affect the advantageous properties inherent to the mixed ester of the cellulose derivative. In addition to the above described dipping method for shaping the capsule shells, any other conventional shaping methods can be used such as compression molding under heating.

In the following, the preparation of the cellulose derivative for shaping the capsule shells used in the inventive rectally applicable medicament capsules is described in detail by way of examples along with the characterization of the cellulose derivatives and the capsule shells. In the following, parts are all given by parts by weight.

Preparation 1

Into a reaction vessel equipped with a stirrer were introduced 100 parts of glacial acetic acid and 20 parts of sodium acetate together with a cellulose ether, succinic anhydride and an anhydride of an aliphatic monocarboxylic acid of the kinds and in amounts as indicated in Table 1 below and the esterification reaction was conducted by agitating the reaction mixture for 3 hours at 85° C. Then, water was added to the reaction mixture to precipitate the reaction product which was taken by filtration, washed with water and dried to give a mixed ester of the cellulose ether containing acidic succinyl groups and aliphatic monoacyl groups. The degrees of substitution, D.S., of these ester groups were as summarized in Table 1.

The cellulose ether compounds as the starting materials used in this preparation and denoted by abridgements in Table 1 were as follows.

TABLE 1

| Sample No. | Starting materials | | | | Product | |
|---|---|---|---|---|---|---|
| | Cellulose ether | | Succinic anhydride, parts | Monocarboxylic acid anhydride | | D.S. of acidic succinyl groups | D.S. of aliphatic monoacyl groups |
| | Compound | Parts | | Compound | Parts | | |
| 1 | HPC | 20 | 4 | Acetic anhydride | 20 | 0.20 | 0.86 |
| 2. | HPMC | 20 | 6 | Acetic anhydride | 32 | 0.25 | 0.57 |
| 3. | HEHPA | 20 | 6 | Propionic anhydride | 40 | 0.30 | 0.85 |

HPC: hydroxypropylcellulose, the average number of substitution with hydroxypropoxyl groups per glucose unit 3.0
HPMC: hydroxypropyl methylcellulose, the average numbers of substitution with hydroxypropoxyl groups and methoxy groups per glucose unit 0.27 and 1.82, respectively
HEHPC: hydroxyethyl hydroxypropylcellulose, the average numbers of substitution with hydroxyethoxy groups and hydroxypropoxyl groups per glucose unit 2.5 and 0.32, respectively In the next place, the above prepared three samples were examined for the stability against hydrolysis and the elongation of the films shaped therefrom along with two kinds of comparative samples No. 4 which was a cellulose acetate phthalate, CAP, having the average degrees of substitution with acetyl groups and phthaloyl groups per glucose unit of 1.84 and 0.76, respectively, and No. 5 which was a hydroxypropyl methylcellulose phthalate, HPMCP, having the average degrees of substitution with hydroxypropoxyl groups, methoxy groups and phthaloyl groups per glucose unit of 0.22, 0.72 and 0.68, respectively. The results are shown in Table 2 below.

Test procedures for the stability against hydrolysis:

(a) Determination of free aliphatic monocarboxylic acid The cellulose derivative kept standing for 6 days or 12 days in atmospheric conditions of 100% relative humidity at 60° C. was subjected to extraction with diethyl ether for 5 hours in a Soxhlet extractor and the aliphatic monocarboxylic acid contained in the ether extract was determined by the gas chromatography.

(b) Determination of free acids other than the aliphatic monocarboxylic acid

The cellulose derivative kept standing in the same atmospheric conditions as above was dissolved in a 1:1 by volume mixed solvent of methylene chloride and methyl alcohol and further admixed with n-hexane. The solution was then extracted with water and the overall amount of the free acids in the water extract was determined by titration with a 0.1 N aqueous solution of sodium hydroxide and the amount of the free acids other than the aliphatic monocarboxylic acid was obtained by the difference between this value and the amount of the free aliphatic monocarboxylic acid obtained in (a) above.

Measurement of the elongation of the films:

Films were prepared by the casting method from a solution of the cellulose derivative dissolved in a 1:1 by volume mixed solvent of methylene chloride and methyl alcohol. Measurement of the elongation was performed on an automatic recording tensile tester at 25° C.

TABLE 2

| Sample No. | Stability against hydrolysis, % by weight of free acid | | | | Elongation of film, % |
|---|---|---|---|---|---|
| | After 6 days | | After 12 days | | |
| | (a) | (b) | (a) | (b) | |
| 1 | 0.3 | 0.1 | 0.6 | 0.2 | 20 |
| 2 | 0.5 | 0.4 | 0.7 | 0.5 | 10 |
| 3 | 0.7 | 0.4 | 0.6 | 0.4 | 10 |
| 4 | 7.0 | 9.3 | 11.0 | 13.2 | 4 |
| 5 | — | 3.1 | — | 3.5 | 3 |

(a): free aliphatic monocarboxylic acid (see test procedure (a))
(b): free acids other than aliphatic monocarboxylic acid (see test procedure (b))

Preparation 2

Following is a description of the preparation of hard capsule shells shaped of the above described mixed esters of the cellulose derivatives as the base material. The capsules were subjected to the test of the disintegrability to give the results shown in Table 3 below.

A viscous dipping solution was prepared by dissolving 90 g of the Sample No. 2 prepared in Preparation 1 above in 210 g of a 6:4 by volume mixed solvent of acetone and ethyl alcohol followed by defoaming by standing at room temperature.

A molding pin either for capsule cap or for capsule body of the size No. 0 after mold-release treatment was dipped in the above prepared dipping solution and then gradually pulled up from the solution to form a film of the viscous solution adhering around the molding pin. Complete drying of the liquid film around the molding pin at 40° to 42° C. gave a capsule shell half having a wall thickness of 150 μm which was demounted from the molding pin and finished to a clear capsule shell half rich in pliability.

A capsule made by coupling the above prepared capsule cap and body was filled with lactose powder and sealed around the coupling portion with the same viscous solution of the cellulose derivative. The disintegrability of the thus prepared capsules was tested in the first and the second solutions having a pH of 1.2 or 7.5, respectively, according to the Ninth Revised Japanese Pharmacopoeia or the McIlvaine buffer solutions having a pH of 4.5, 5.0, 5.5 or 6.0. The dissolvability behavior of the capsules in each of the test solutions was as follows.

(i) No noticeable changes within 2 hours in the first solution of pharmacopoeia at pH 1.2.

(ii) No noticeable changes within 2 hours in the McIlvaine buffer solution at pH 4.5.

(iii) No noticeable changes within 2 hours in the McIlvaine buffer solution at pH 5.0.

(iv) The capsule was dissolved and broken to release the content after 20 to 25 minutes in the McIlvaine buffer solution at pH 5.5.

(v) The capsule was dissolved and broken to release the content after 8 to 10 minutes in the McIlvaine buffer solution at pH 6.0.

(vi) The capsule was dissolved and broken to release the content after 6 to 9 minutes in the second solution of pharmacopoeia at pH 7.5.

Preparation 3

Capsule shells having a wall thicknes of 150 μm were prepared in the same manner as in Preparation 2 above except that dipping solution used for pin molding was a solution of 20 g of the Sample No. 1 prepared in Preparation 1 in 80 g of a 8:2 by volume mixed solvent of ethyl alcohol and water. The capsules were also clear and rich in pliability.

The dissolvability test of the capsules was conducted in the same manner as above with the first and the second solutions according to the pharmacopoeia to give the results as follows.

(vii) No noticeable changes within 2 hours in the first solution at pH 1.2.

(viii) The capsule was dissolved and broken to release the content after 15 to 20 minutes in the second solution at pH 7.5.

Preparation 4

Capsule shells having a wall thickness of 150 μm were prepared in the same manner as in Preparation 2 above except that the viscous dipping solution used for pin molding was a solution of 25 g of the Sample No. 3 prepared in Preparation 1 in 75 g of a 1:1 by volume mixed solvent of acetone and ethyleneglycol monomethyl ether. The capsules were also clear and rich in pliability.

The dissolvability test of the capsule was conducted in the same manner as above with the first and the second solutions according to the pharmacopoeia to give the results as follows.

(ix) No noticeable changes within 2 hours in the first solution at pH 1.2.

(x) The capsule was dissolved and broken to release the content after 15 to 25 minutes in the second solution at pH 7.5.

Preparation 5

Capsule shells of No. 0 size were prepared with a hydroxypropyl methylcellulose acetate succinate in a similar manner to Preparation 2 in two different wall thickness of (A) 150 μm and (B) 100 μm each weighing 125 mg or 110 mg, respectively, for the capsule cap and body together.

The dissolvability behavior of each of the above prepared capsule filled with barium sulfate was examined in a test apparatus for disintegration specified in the pharmacopoeia but without the auxiliary plastic disk to give the results graphically illustrated in FIG. 1.

As is clear from the Figure, the capsules were stable at pH 5.0 for 2 hours or longer irrespective of the wall thickness. The dissolution of the capsules took place only at a pH 5.5 or higher and was considerably rapid at a pH of 6.0 or higher with somwhat larger velocities for the capsules of smaller wall thickness than for those with larger wall thickness.

Simulating In Vivo Test

Simulating capsules were prepared by filling the comparative capsules A and B prepared in Preparation 5 above with a 30% by weight suspension of barium sulfate in water or in sesame oil as a contrast medium. The capsules were inserted each into the rectum about 3 cm deep from the anus of a male rabbit having a body weight of about 3 kg after a fasting period of 17 hours and traced roentgenographically with soft X-rays by use of an apparatus Model Softex CMEW-2, manufactured by Nippon Softex Co., Japan, to examine the in vivo dissolvability behavior of the capsules. The results of the average time in minutes for the dissolution of the capsules in the rabbit recta were as shown in Table 3 below.

TABLE 3

| Content of capsule | Capsule A | Capsule B |
|---|---|---|
| Barium sulfate/water suspension | 40 minutes | 20 minutes |
| Barium sulfate/sesame oil suspension | 95 minutes | 50 minutes |

The time to the dissolution of the capsule A was about twice as long as that with the capsule B in parallel with the general trend in the in vitro test described in Preparation 5 and illustrated in FIG. 1. The aqueous suspension filling the capsule apparently accelerated the dissolution of the capsule in comparison with the suspension in sesame oil.

As is understood from the above given description of the preparations and the simulating in vivo test, the medicament capsules according to the present invention are very suitable as a dosage form for rectal application. It may be concluded from the above results that (a) the wall thickness of the capsule in the invention can be the same as or slightly smaller than in the ordinary capsules for oral administration provided no troubles are caused in rectal application and (b) the form of the capsule is desirably conical or cannonball-like in order to facilitate rectal application but the conventional capsule assemblage of cap and body coupled together having dome-like or semispherical closed ends are well suitable for the purpose.

The medicines to fill the inventive medicament capsules are not limited to particular ones and may include all kinds of medicines hitherto formulated in suppositories as the therapeutically effective ingredient such as antipyretics, anodynes, antiphlogistics, antispasmodics, antibiotics, antituberculosis agents, astringents, local anesthetics, bactericides, laxatives and the like.

As is understood from the foregoing, the inventive medicamant capsules are practically very advantageous because the dosage form preparation is very easy and no special care is needed in the storage thereof by virtue of the utilization of a hard capsule made of a specific material having excellent stability. These advantages will be more clearly understood when comparisons are made between the characteristics of the inventive medicament capsules and the conventional suppositories and gelatin-made hard and soft capsules as tabulated below in Table 4.

TABLE 4

| Dosage form for rectal application | Inventive medicament capsule | Suppository | Gelatin-made soft capsule | Gelatin-made hard capsule |
| --- | --- | --- | --- | --- |
| Temperature condition in storage | Room temperature | Cool place | Room temperature | Room temperature |
| Stability of powdery medicine | Good | Fair | Fair | Good |
| Applicability Aqueous of liquid | Yes | No | No | No |
| medicine Oily | Yes | Yes | Yes | Yes |
| Filling work with the medicine | Manual or machine work | Machine work | Machine work | Manual or machine work |
| Applicability of acidic medicine | Yes | Yes | No | No |

Dose Test 1

In this dose test and hereunder, medicament capsules were prepared of the capsule shells having a wall thickness of 100 μm obtained in Preparation 5. Medicament capsules were prepared by filling the capsules with a suspension of sulfamethoxazole as the test ingredient in water or in sesame oil in such an amount that each capsule contained 240 mg of the effective ingredient. In parallel, suppositories were prepared as a dosage form for control by casting a uniform blend of sulfamethoxazole in a molten suppository base at 50° C., which was a mixture of mono-, di- and triglycerides of saturated fatty acids having from 12 to 18 carbon atoms in a molecule (Witepsol, a product by Dynamit Nobel Co.) into a conventional suppository form. Each piece of the suppositories also contained 240 mg of the effective ingredient. Each a piece of the above test capsules and the control suppositories was composed of the respective materials in amounts indicated in Table 5 in mg.

TABLE 5

|  | Test capsule B-1 | Test capsule B-2 | Control suppository |
| --- | --- | --- | --- |
| Sulfamethoxazole | 240 mg | 240 mg | 240 mg |
| Water | 500 | — | — |
| Sesame oil | — | 390 | — |
| Capsule | 110 | 110 | — |
| Witepsol | — | — | 760 |
| Total | 850 | 740 | 1000 |

Figure 2:
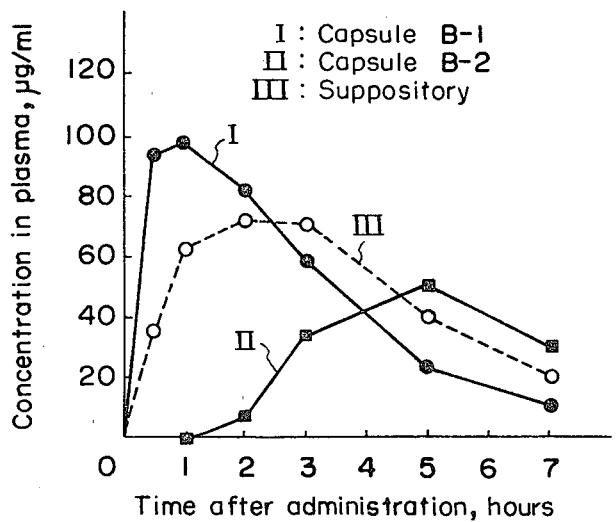
FIG. 2 shows the changes in the concentration of sulfamethoxazole in blood plasma of rabbits administrated by rectal application with the medicine in the form of the inventive medicament capsule containing the same as a function of time.

Each of the above prepared capsules and suppositories was inserted to the rectum about 3 cm deep from the anus of a male rabbit having a body weight of 2.9 to 3.1 kg after a fasting period of 17 hours and blood was taken periodically from the vein on the earlobe. Blood plasma was ontained from the blood by centrifugal separation and the concentration of sulfamethoxazole in the plasma was determined to give the results as plotted in FIG. 2.

As is clear from the results, the inventive capsule containing the aqueous suspension of the medicine gave a larger velocity of increase in the concentration of the medicine in the plasma as well as a higher maximum concentration than the Witepsol-based suppository. These results support the practical advantages of the rectally applicable medicament capsules of the present invention over the conventional suppository as a dosage form. When the aqueous suspension contained in the capsule was replaced with a suspension in sesame oil, retardation was noted in the rate of absorption of the effective ingredient though not to an extent of impracticality.

Dose Test 2

A pasty mixture was prepared by uniformly blending 50 g of sulfamethoxazole and 30 g of olive oil and a capsule shell having a wall thickness of 100 μm obtained in Preparation 5 was filled with 800 mg of the paste containing 500 mg of the effective ingredient to give a rectally applicable medicament capsule which was subjected to the animal test in the same manner as in Dose Test 1 above to give equally good results.

Dose Test 3

A pasty mixture was prepared by uniformly blending 22.5 g of sulfamethoxazole and 36 g of olive oil and a capsule shell of No. 2 size having a wall thickness of 100 μm prepared in the same manner as in Preparation 5 was filled with 390 mg of the paste containing 150 mg of the effective ingredient to give a rectally applicable medicament capsule which was subjected to the animal test in the same manner as in Dose Test 1 to give equally good results.

Dose Test 4

An oily suspension was prepared by uniformly blending 75 g of aspirin, 141 g of olive oil and further 7.8 g of a finely divided silicic anhydride and a capsule shell obtained in Preparation 5 was filled with 746 mg of the suspension containing 250 mg of aspirin to give a rectally applicable medicament capsule which was subjected to the animal test in a manner similar to Dose Test 1 above to give equally good results.

Dose Test 5

An oily suspension was prepared by uniformly blending 50 mg of betamethasone, 63.6 g of sesame oil and further 2.6 g of a finely divided silicic anhydride and a capsule shell of No. 0 size obtained in Preparation 5 was filled with 663 mg of the suspension containing 0.5 mg of the effective ingredient to give a rectally applicable medicament capsule which was subjected to the animal test in a manner similar to Dose Test 1 above to give equally good results.

As is understood from the above description and the results of the dose tests, the medicament capsules according to the present invention are very advantageous over the conventional dosage forms for rectal application in that a wide versatility is obtained in the form of the medicicines to be contained in the capsule shells including any kind of aqueous liquid medicines such as aqueous solutions, aqueous suspensions, emulsions and the like which hitherto have been considered to be quite unsuitable for rectal application.

What is claimed is:

1. A medicament capsule for rectal application which comprises
   (a) a hard capsule shell made of a mixed ester of a cellulose ether selected from the group consisting of alkylcelluloses, hydroxyalkylcelluloses and hydroxyalkyl alkylcelluloses and esterified with aliphatic monoacyl groups and acidic succinyl groups, and
   (b) a therapeutically effective ingredient capable of being rectally absorbed and encapsulated in the daid hard capsule shell.

2. The medicament capsule for rectal application as claimed in claim 1 wherein the alkylcellulose is selected from the group consisting of methylcellulose, ethylcellulose and propylcellulose.

3. The medicament capsule for rectal application as claimed in claim 1 wherein the hydroxyalkylcellulose is selected from the group consisting of hydroxyethylcellulose, hydroxypropylcellulose, hydroxyethyl hydroxypropylcellulose and hydroxyethyl hydroxybutylcellulose.

4. The medicament capsule for rectal application as claimed in claim 1 wherein the hydroxyalkyl alkylcellulose is selected from the group consisting of hydroxyethyl methylcellulose, hydroxyethyl ethylcellulose, hydroxypropyl methylcellulose, hydroxypropyl ethylcellulose, hydroxybutyl methylcellulose, hydroxybutyl ethylcellulose and hydroxyethyl hydroxypropyl methylcellulose.

5. The medicament capsule for rectal application as claimed in claim 1 wherein the aliphatic monoacyl groups is selected from the group consisting of acetyl, propionyl, butyryl and valeryl groups.

6. The medicament capsule for rectal application as claimed in claim 1 wherein the degrees of substitution with the aliphatic monoacyl groups and acidic succinyl groups in the mixed ester of the cellulose ether are at least 0.05 and at least 0.1, respectively, per glucose unit.

7. The medicament capsule for rectal application as claimed in claim 1 wherein the hard capsule shell has a wall thickness in the range from 100 to 150 $\mu$m.

* * * * *